US010041926B2

(12) United States Patent
Miao et al.

(10) Patent No.: US 10,041,926 B2
(45) Date of Patent: Aug. 7, 2018

(54) METHOD FOR PREDICTING TOTAL PETROLEUM HYDROCARBON CONCENTRATION IN SOILS

(71) Applicant: Chevron U.S.A. Inc., San Ramon, CA (US)

(72) Inventors: Toni Zhang Miao, Orinda, CA (US); Rachel Mohler, Pinole, CA (US); Deyuan Kong, San Ramon, CA (US); Ajit Ramachandra Pradhan, Walnut Creek, CA (US); Michael E. Moir, San Rafael, CA (US); Thomas Hoelen, Berkeley, CA (US)

(73) Assignee: CHEVRON U.S.A. INC., San Ramon, CA (US)

( * ) Notice: Subject to any disclaimer, the term of this patent is extended or adjusted under 35 U.S.C. 154(b) by 0 days.

(21) Appl. No.: 15/648,028

(22) Filed: Jul. 12, 2017

(65) Prior Publication Data

US 2018/0017540 A1    Jan. 18, 2018

Related U.S. Application Data

(60) Provisional application No. 62/362,145, filed on Jul. 14, 2016.

(51) Int. Cl.
*G01N 33/24* (2006.01)
*G01N 21/3563* (2014.01)
(Continued)

(52) U.S. Cl.
CPC ....... *G01N 33/241* (2013.01); *G01N 21/3563* (2013.01); *G01N 21/552* (2013.01); *G01N 2030/025* (2013.01); *G01N 2201/129* (2013.01)

(58) Field of Classification Search
CPC . G01N 33/241; G01N 21/3563; G01N 21/552
See application file for complete search history.

(56) References Cited

U.S. PATENT DOCUMENTS

| 2012/0226653 | A1* | 9/2012 | McLaughlin | ........ G01N 21/359 706/52 |
| 2017/0160136 | A1* | 6/2017 | Spartz | ....................... G01J 3/42 |
| 2017/0299431 | A1* | 10/2017 | Pastore | ................. G01J 3/0264 |

OTHER PUBLICATIONS

Linker Raphael [(2011) Application of FTIR Spectroscopy to Agricultural Soils Analysis, Fourier Transforms—New Analytical Approaches and FTIR Strategies, Prof. Goran Nikolic (Ed.), ISBN: 978-953-307-232-6, InTech, Available from: http://www.intechopen.com/books/fourier-transforms-new-analytical-approaches-and-ftirstrategies/application-of-ftir-sp.*

* cited by examiner

*Primary Examiner* — Hugh H Maupin
(74) *Attorney, Agent, or Firm* — Karen R. DiDomenicis

(57) ABSTRACT

Disclosed is a method for generating a site specific model for predicting TPH concentration in soil. The method includes dividing a plurality of soil samples taken from a field site into two sets of samples. One set is analyzed using GC-FID, and the other set is analyzed using a handheld FTIR spectrometer with an ATR window to obtain FTIR-ATR absorbance data. Partial least squares regression analysis is used to correlate the GC-FID TPH concentration data with the absorbance data to generate a calibration model. The model is validated with soil samples having unknown TPH concentration. The model is used to predict the TPH concentration of soil samples taken from the field site analyzed using the handheld Fourier transform-infrared spectrometer to obtain FTIR-ATR absorbance data for the soil samples. During all absorbance measurements, each of the soil samples has a moisture content of 1 to 30 wt % and each (Continued)

sample is pressed against the ATR window with sufficient pressure to ensure intimate contact between the sample and the window.

6 Claims, 2 Drawing Sheets

(51) Int. Cl.
  *G01N 21/552* (2014.01)
  *G01N 30/02* (2006.01)

METHOD FOR PREDICTING TOTAL PETROLEUM HYDROCARBON CONCENTRATION IN SOILS

FIELD

The present disclosure relates to methods for estimating total petroleum hydrocarbons (TPH) concentration in soil samples using attenuated total reflectance (ATR) spectroscopy data and prediction models generated by Fourier transform infrared (FTIR) spectroscopy, in particular using mid-infrared spectroscopy and partial least squares (PLS) analysis.

BACKGROUND

Measurements of total petroleum hydrocarbons (TPH) in soils are often required to assess environmental remedial endpoints and satisfy regulatory requirements. Soil TPH concentrations can be obtained in analytical laboratories, typically using gas chromatography (GC) such as GC with a flame ionization detector (GC-FID). However, lengthy turnaround times of weeks to months can cause significant delays in field operations, e.g., during soil treatment processes, when such laboratory techniques are used. A method that can quickly generate TPH concentration in soil of sufficient quality to make real-time field decisions would be useful to decrease the time requirements for soil remediation, reduce the number of samples that have to be analyzed by a laboratory, allow for quick follow-up sampling during site assessment and/or reduce uncertainty due to increased sampling density, ultimately reducing the overall project cost. Field test kits for soil TPH analyses are commercially available, but typically require a solvent extraction step, which makes them time consuming and complicated to use in the field. Near- and mid-DRIFT (Diffuse Reflectance Infrared Fourier Transform) using portable spectrometers have also been shown to give promising results for estimating TPH concentration in soils. Reflectance IR spectra can be acquired easily and rapidly because of the high sensitivity of alkyl-$CH_3$ vibrational group. However, these methods require a time-consuming step to dry each sample.

In attenuated total reflectance (ATR) Fourier transform infrared spectroscopy, also referred to interchangeably as FTIR-ATR and ATR-FTIR, infrared light is introduced into a prism at an angle exceeding a critical angle for internal reflection. An evanescent wave is produced at the surface on which the sample is supported, extending into the sample. The evanescent wave is distorted by the sample resulting in a spectrum. The spectrum is measured and subjected to a Fourier transform.

Despite advances in the field, there still exists a need for an alternative method for estimating total petroleum hydrocarbons concentration in contaminated soils quickly and simply, without the need for time consuming sample preparation.

SUMMARY

In one aspect, a method is provided for generating a site specific model for predicting total petroleum hydrocarbon (TPH) concentration in soil. The method includes homogenizing and dividing a plurality of soil samples taken from a field site into a first set of soil samples and a second set of soil samples. The first set of samples is analyzed using gas chromatography with a flame ionization detector (GC-FID) in a laboratory to obtain GC-FID TPH concentration data. The second set of samples is analyzed using a handheld Fourier transform-infrared (FTIR) spectrometer with an attenuated total reflectance (ATR) window to obtain FTIR-ATR absorbance data. Partial least squares regression analysis is used to correlate the GC-FID TPH concentration data with the FTIR-ATR absorbance data to generate a calibration model which is the site specific predictive model for TPH concentration for the field site. To validate the model, a plurality of validation soil samples having unknown TPH concentration is analyzed using the handheld Fourier transform-infrared spectrometer to obtain FTIR-ATR absorbance data for the validation soil samples. During all FTIR-ATR absorbance measurements, each of the soil samples has a moisture content of from 1 wt % to 30 wt % and each sample is pressed against the ATR window with sufficient pressure to ensure intimate contact between the sample and the ATR window. The FTIR-ATR absorbance data for the validation soil samples are used to predict the TPH concentration of the validation soil samples using the site specific predictive model. The TPH concentration of the validation soil samples is measured using GC-FID. The predicted TPH concentration of the validation soil samples is compared with the TPH concentration of the validation soil samples as measured using GC-FID.

In another aspect, a soil sample as a validation sample taken from the field site having an unknown TPH concentration is analyzed using the handheld Fourier transform-infrared spectrometer to obtain FTIR-ATR absorbance data for the soil sample. The site specific predictive model generated using the method described above is then used to predict the TPH concentration of the soil sample.

BRIEF DESCRIPTION OF THE DRAWINGS

These and other objects, features and advantages of the present invention will become better understood with reference to the following description, appended claims and accompanying drawings. The drawings are not considered limiting of the scope of the appended claims. The elements shown in the drawings are not necessarily to scale. Reference numerals designate like or corresponding, but not necessarily identical, elements.

DETAILED DESCRIPTION

Figure 1:
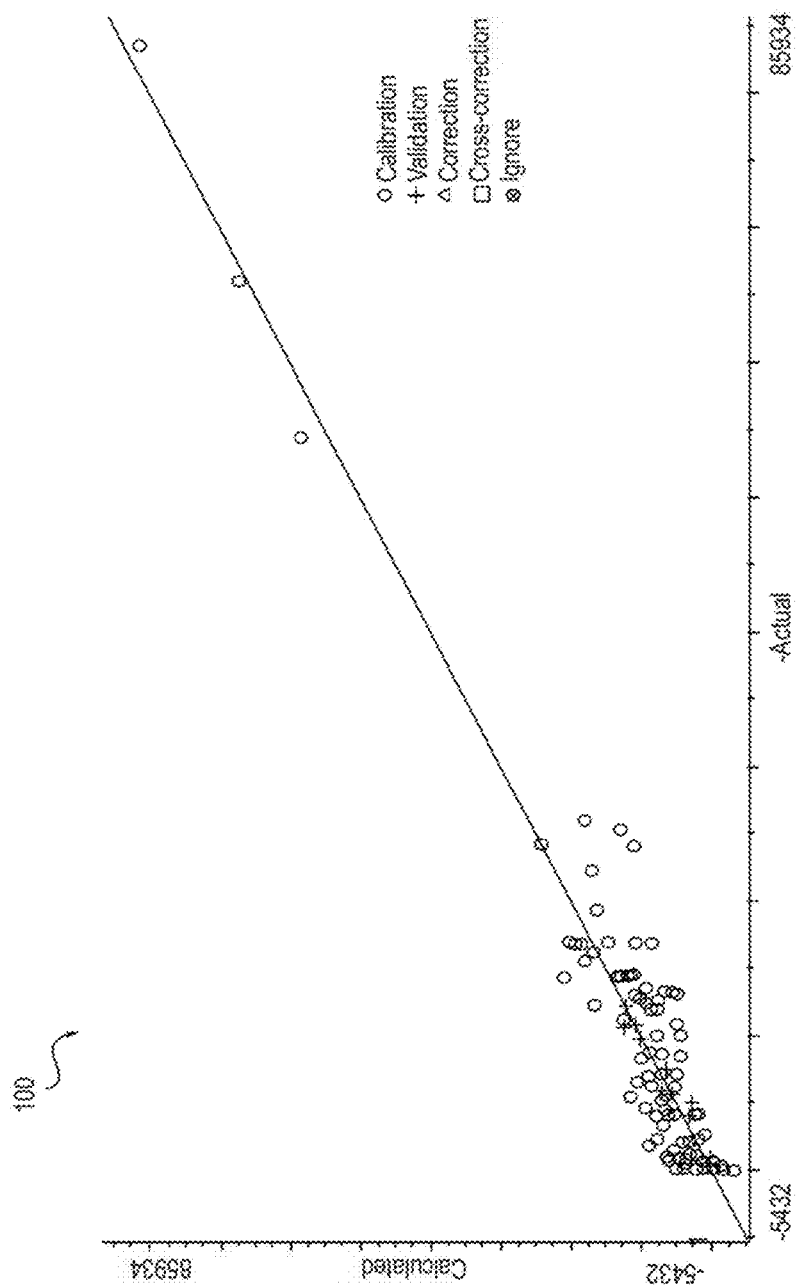
FIG. 1 is a graph illustrating an ATR-IR chemometric model of calculated TPH vs. actual TPH.

In some embodiments, a method using ATR mid-infrared spectroscopy is disclosed as a rapid screening tool for predicting total petroleum hydrocarbon (TPH) concentrations in contaminated soils. In some embodiments, the contaminated soil contains crude oil.

In one aspect, a method is provided for generating a site specific predictive model for predicting total petroleum hydrocarbon (TPH) concentration in soil. The method includes homogenizing and dividing a plurality of soil samples taken from a field site into a first set of soil samples and a second set of soil samples such that the first and second sets of soil samples are substantially equivalent for purposes of predictive model calibration.

The first set of samples is analyzed using gas chromatography with a flame ionization detector (GC-FID) in a laboratory to obtain GC-FID TPH concentration data. Test method EPA 8015 is used for measuring TPH concentrations in the $C_{10-36}$ range.

The second set of samples is analyzed using a handheld Fourier transform-infrared (FTIR) spectrometer with an attenuated total reflectance (ATR) window to obtain FTIR-ATR absorbance data. The methods disclosed use a handheld spectrometer such as a handheld Fourier transform-infrared (FTIR) spectrometer with attenuated total reflectance (ATR) window. An example of a suitable spectrometer is the 4100 ExoScan Series Fourier transform infrared (FTIR) Spectrometer with ATR interface (e.g., spherical diamond) (available from Agilent Technologies, Santa Clara, Calif.). During all FTIR-ATR absorbance measurements, each sample is pressed against the ATR window with sufficient pressure to ensure intimate contact between the sample and the ATR window. Pressure sufficient to deform the sample will increase the extent of sample contact with the ATR window and result in good FTIR-ATR absorbance of the sample.

The methods disclosed can advantageously be applied to neat whole soils having from 1 to 30 wt % water content without the need for solvent extraction from the samples or drying of the samples.

In some embodiments, multiple replicate spectra of FTIR-ATR absorbance data are obtained for separate soil samples. The FTIR-ATR absorbance data of the replicate spectra are averaged to provide a composite spectrum.

Partial least squares regression analysis is used to correlate the GC-FID TPH concentration data with the FTIR-ATR absorbance data to generate a calibration model which is the site specific predictive model for TPH concentration for the field site. In some embodiments, the peak area of the FTIR-ATR absorbance data in the C—H stretching frequency range of from 2700 to 3100 $cm^{-1}$ and/or of the FTIR-ATR absorbance data in the C—$CH_2$ stretching frequency range of from 1350 to 1450 $cm^{-1}$ is integrated to provide an indication of TPH concentration based on the partial least squares regression analysis to correlate the GC-FID TPH concentration data with the FTIR-ATR absorbance data. In some embodiments, means centering and first derivative techniques are used to remove noise from the obtained absorbance data.

To validate the model, a plurality of validation soil samples having unknown TPH concentration is analyzed using the handheld Fourier transform-infrared spectrometer to obtain FTIR-ATR measurements. During such FTIR-ATR absorbance measurements, each of the soil samples has a moisture content of from 1 wt % to 30 wt % and each sample is pressed against the ATR window with sufficient pressure to ensure intimate contact between the sample and the ATR window. The FTIR-ATR absorbance data for the validation soil samples are used to predict the TPH concentration of the validation soil samples using the site specific predictive model. The TPH concentration of the validation soil samples is measured using GC-FID. Calculated FTIR-ATR data and measured GC-FID data are subjected to regression analysis and the coefficient of determination, $R^2$, is determined to indicate the ability of the calibration model to predict and quantify TPH concentration in soil samples taken from the same field site. The $R^2$ value indicates whether the site specific chemometric model can provide acceptable prediction of TPH concentration in soil at field site.

Once the model is validated, the model can be used to predict TPH concentrations of soil samples having unknown TPH concentration where the samples are taken from the same field site from whence the soil samples came to develop the model. For example, a soil sample can be taken from the field site and analyzed using the handheld Fourier transform-infrared spectrometer to obtain FTIR-ATR absorbance data. Using the site specific predictive model, the TPH concentration of the soil sample is predicted. Again, during all FTIR-ATR absorbance measurements, each of the soil samples has a moisture content of from 1 wt % to 30 wt % and each sample is pressed against the ATR window with sufficient pressure to ensure intimate contact between the sample and the ATR window.

EXAMPLES

Crude oil impacted samples, consisting mostly of dune sand, were collected from an excavation site. A total of 100 samples were collected. Approximately 500 g of soil was collected for each sample and sieved in the field to remove large material such as gravel, pebbles and roots.

The samples were homogenized and divided into split samples in a laboratory. 75 samples were divided into split samples for developing a calibration model, also referred to as calibration samples. The remaining 25 samples of the total 100 samples were reserved for model validation; these 19 samples are also referred to as validation samples.

A 4100 ExoScan Series Fourier transform infrared (FTIR) Spectrometer with ATR spherical diamond interface (available from Agilent Technologies, Santa Clara, Calif.) was used for the IR measurements of one half of the calibration samples, at frequencies of from 2700 to 3100 cm-1 of C—H stretches. TPH of the other half of the calibration samples was measured by GC-FID at a reference laboratory. Gas chromatography with a flame ionization detector (GC-FID) was used according to test method EPA 8015 for the GC-FID measurements to detect C10-36 concentrations.

The IR and GC-FID results for the 75 samples were used to build a site-specific chemometric model to calibrate the IR spectrometer. The site-specific model was developed using a partial least squares (PLS) technique to develop model equations for the quantification of TPH concentration from the absorbance data. The results were compared to those obtained by traditional methods (TPH by GC-FID) at an EPA-approved third party laboratory.

TPH values in soil samples, as predicted (or calculated) by the site specific chemometric model, shows a good agreement with GC-FID data with an $R^2$ of 0.96 as depicted in FIG. 1. Evaluation of the root mean square error suggests that the lower detection threshold for the ATR using the site specific model was approximately 2000 ppm, indicating that concentrations reported below this threshold should not be quantified.

Figure 2:
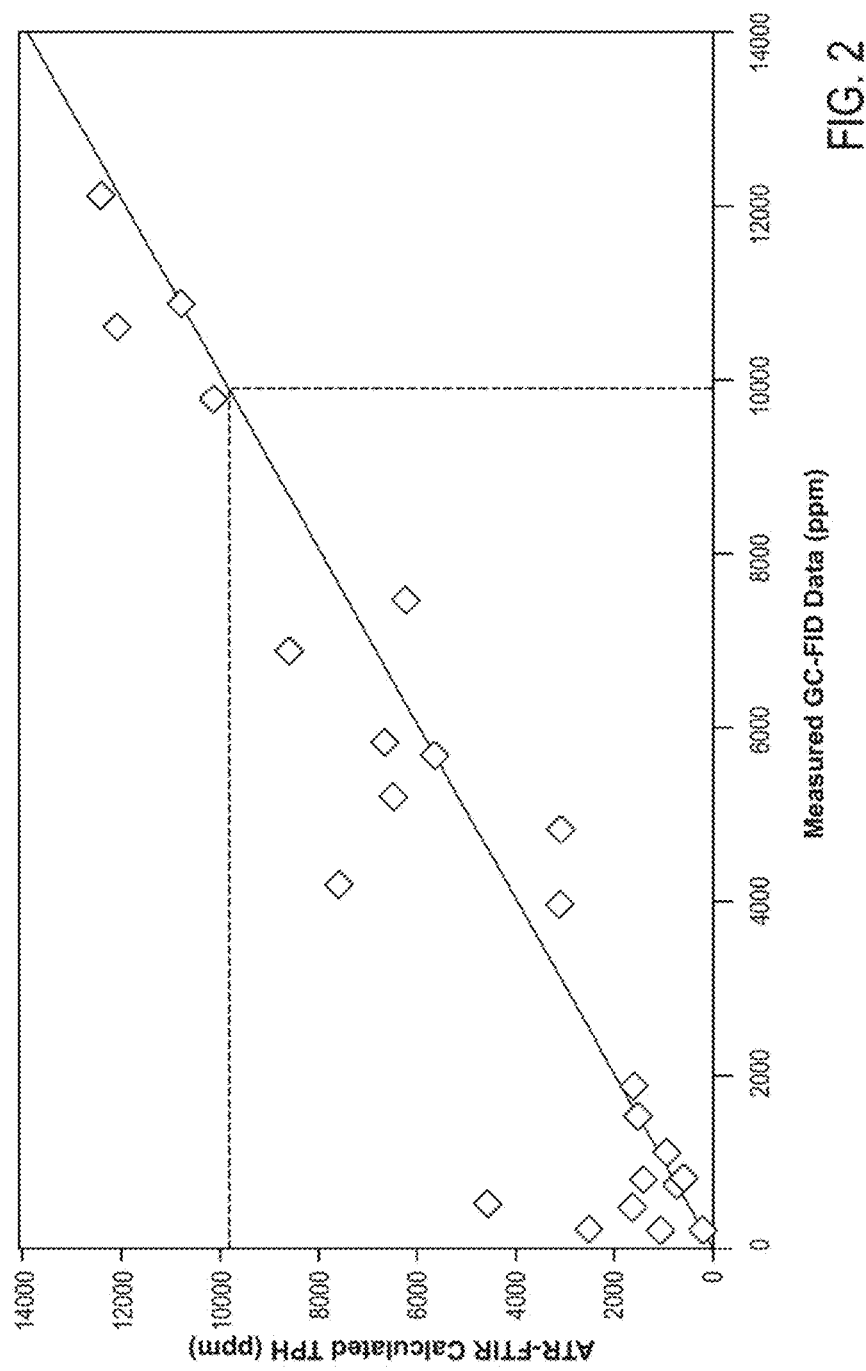
FIG. 2 is a graph illustrating a validation test of calculated ATR-IR vs. GC-FID data for validation soil samples.

To verify the performance of the calibrated chemometric model to quantify TPH concentrations for unknown samples, the calculated TPH values of validation samples were compared with GC-FID data as shown in FIG. 2. For the validation samples (25 samples) validation data showed a good agreement between the by GC-FID measured value vs. IR calculated, with an $R^2$ of 0.94 indicating that the chemometric model could provide a suitable prediction of TPH concentration in soil at the field site. Evaluation of the data below 2,000 ppm showed that the ATR-IR produced one false positive and no false negative. If accuracy below 2000 ppm is needed then the more low level of soil samples can be tested to refine further the model to get lower detection limit.

Upon investigation of impact of moisture content on FTIR-ATR measurements, 10-30 wt % range of moisture content have been tested on two soil samples (A and B) with addition of water. The C—H stretch vibration band has been monitored and measured with increasing percentage of moisture content. Surprisingly both peak height and area were not affected by the moisture content as shown in Table 1.

TABLE 1

| Sample ID | Moisture content (%) | C—H Stretching Peak Height | C—H Stretching Peak Height with Water Signal Baseline | CH Stretching Peak Area with Water Signal Baseline |
|---|---|---|---|---|
| Sample A | | | | |
| 1 | 13.04 | 0.03 | 0.01 | 0.59 |
| 2 | 28.58 | 0.03 | 0.01 | 0.51 |
| 3 | 21.36 | 0.03 | 0.01 | 0.54 |
| 4 | 23.60 | 0.02 | 0.01 | 0.60 |
| 5 | 33.19 | 0.03 | 0.01 | 0.52 |
| Sample B | | | | |
| 1 | 15.82 | 0.02 | 0.01 | 0.47 |
| 2 | 20.69 | 0.02 | 0.01 | 0.79 |
| 3 | 24.37 | 0.03 | 0.01 | 0.43 |
| 4 | 29.87 | 0.03 | 0.01 | 0.43 |
| 5 | 33.22 | 0.03 | 0.01 | 0.67 |

The results indicate that the handheld FTIR-ATR provides a suitable method for field screening of TPH concentrations above approximately 2000 ppm. TPH can be determined in soil in minutes as compared with hours using current methods. A good correlation was observed for TPH concentrations above approximately 2,000 ppm, suggesting that the method can be used to identify samples with relatively high TPH concentrations ranging from 3000 ppm to 2 wt %. Soils with TPH concentrations below approximately 2000 ppm of TPH should be analyzed by different method if quantification below that level is desired.

For the purposes of this specification and appended claims, unless otherwise indicated, all numbers expressing quantities, percentages or proportions, and other numerical values used in the specification and claims are to be understood as being modified in all instances by the term "about." Accordingly, unless indicated to the contrary, the numerical parameters set forth in the following specification and attached claims are approximations that can vary depending upon the desired properties sought to be obtained by the present invention. It is noted that, as used in this specification and the appended claims, the singular forms "a," "an," and "the," include plural references unless expressly and unequivocally limited to one referent.

Unless otherwise specified, the recitation of a genus of elements, materials or other components, from which an individual component or mixture of components can be selected, is intended to include all possible sub-generic combinations of the listed components and mixtures thereof. Also, "comprise," "include" and its variants, are intended to be non-limiting, such that recitation of items in a list is not to the exclusion of other like items that may also be useful in the materials, compositions, methods and systems of this invention.

This written description uses examples to disclose the invention, including the best mode, and also to enable any person skilled in the art to make and use the invention. The patentable scope is defined by the claims, and can include other examples that occur to those skilled in the art. Such other examples are intended to be within the scope of the claims if they have structural elements that do not differ from the literal language of the claims, or if they include equivalent structural elements with insubstantial differences from the literal languages of the claims. All citations referred herein are expressly incorporated herein by reference.

From the above description, those skilled in the art will perceive improvements, changes and modifications, which are intended to be covered by the appended claims.

What is claimed is:

1. A method for generating a site specific predictive model for estimating total petroleum hydrocarbon (TPH) concentration in contaminated soil high in water content, the method comprising:
    a. homogenizing and dividing a plurality of soil samples taken from a field site into a first set of soil samples and a second set of soil samples;
    b. analyzing the first set of soil samples using gas chromatography with a flame ionization detector (GC-FID) in a laboratory to obtain GC-FID TPH concentration data;
    c. analyzing the second set of soil samples using a handheld Fourier transform-infrared (FTIR) spectrometer with attenuated total reflectance (ATR) window to obtain FTIR-ATR absorbance data wherein the second set of soil samples have a water content of from 10 wt % to 33 wt % and each of the second set of soil samples is pressed against the ATR window with sufficient pressure to ensure intimate contact between the sample and the ATR window, wherein a plurality of replicate spectra of FTIR-ATR absorbance data are obtained for separate soil samples and the FTIR-ATR absorbance data obtained are an average of the replicate spectra;
    d. applying partial least squares regression analysis to correlate the GC-FID TPH concentration data with the FTIR-ATR absorbance data to generate the site specific predictive model for TPH concentration for the field site including integrating peak area of the FTIR-ATR absorbance data in the C—H stretching frequency range of from 2700 to 3100 $cm^{-1}$ and/or of the FTIR-ATR absorbance data in the C—$CH_2$ stretching frequency range of from 1350 to 1450 $cm^{-1}$ to indicate TPH concentration based on the partial least squares regression analysis to correlate the GC-FID TPH concentration data with the FTIR-ATR absorbance data;
    e. analyzing a plurality of validation soil samples taken from the field site having unknown TPH concentration using the handheld Fourier transform-infrared spectrometer to obtain FTIR-ATR absorbance data for the validation soil samples wherein the validation soil samples have a water content of from 10 wt % to 33 wt % and each of the validation soil samples is pressed against the ATR window with sufficient pressure to ensure intimate contact between the sample and the ATR window;
    f. using the FTIR-ATR absorbance data for the validation soil samples to predict the TPH concentration of the validation soil samples using the site specific predictive model;
    g. measuring the TPH concentration of the validation soil samples using GC-FID; and
    h. comparing the predicted TPH concentration of the validation soil samples with the TPH concentration of the validation soil samples as measured using GC-FID to validate the predictive model.

2. The method of claim 1, further comprising analyzing a soil sample taken from the field site having an unknown TPH concentration using the handheld Fourier transform-infrared spectrometer to obtain FTIR-ATR absorbance data for the soil sample; and using the site specific predictive model to predict the TPH concentration of the soil sample.

3. The method of claim 1 or claim 2, wherein the FTIR-ATR absorbance data obtained is obtained without extraction of solvent from the soil samples.

4. The method of claim 1 or claim 2, wherein the FTIR-ATR absorbance data obtained is obtained without drying the soil samples.

5. The method of claim 1, wherein the applying partial least squares regression analysis further comprises using means centering and first derivative to remove noise from the obtained data.

6. The method of claim 1, wherein the contaminated soil comprises crude oil.

\* \* \* \* \*